United States Patent [19]

Chu et al.

[11] Patent Number: 4,899,007

[45] Date of Patent: Feb. 6, 1990

[54] AROMATIC CONVERSION REACTIONS WITH ZEOLITIC CATALYST COMPOSITION OF IMPROVED SHAPE SELECTIVITY

[75] Inventors: Pochen Chu, West Deptford, N.J.; Francis G. Dwyer, West Chester; Albert B. Schwartz, Philadelphia, both of Pa.

[73] Assignee: Mobil Oil Corporation, New York, N.Y.

[21] Appl. No.: 679,673

[22] Filed: Dec. 10, 1984

Related U.S. Application Data

[63] Continuation-in-part of Ser. No. 533,893, Sep. 21, 1983, abandoned, which is a continuation of Ser. No. 454,302, Dec. 29, 1982, abandoned, which is a continuation of Ser. No. 7,871, Jan. 31, 1979, abandoned.

[51] Int. Cl.$^4$ .................................................. C07C 2/68
[52] U.S. Cl. ...................................... 585/467; 585/470; 585/471
[58] Field of Search .................... 585/470, 467, 471

[56] References Cited

U.S. PATENT DOCUMENTS

| | | | |
|---|---|---|---|
| 3,790,471 | 2/1974 | Argauer et al. | 502/71 |
| 4,016,218 | 4/1977 | Haag et al. | . |
| 4,070,407 | 1/1978 | Haag et al. | . |
| 4,090,981 | 5/1978 | Rodewald | 585/467 |
| 4,136,128 | 1/1979 | Haag et al. | 585/467 |
| 4,146,584 | 3/1979 | Rollmann | 585/467 |
| 4,288,647 | 9/1981 | Chu | 585/470 |
| 4,377,718 | 3/1983 | Sato et al. | 585/467 |

*Primary Examiner*—William R. Dixon, Jr.
*Assistant Examiner*—Maria Reardon Nguyen
*Attorney, Agent, or Firm*—Alexander J. McKillop; Charles J. Speciale; Edward F. Kenehan, Jr.

[57] ABSTRACT

There are provided aromatic conversion reactions for preparation of dialkyl benzenes, such as xylene and ethyltoluene, of enhanced para isomer content with a zeolitic catalyst composition of improved shape selectivity. The catalysts comprise certain zeolites which have been calcined at a high temperature of at least 649° C. (i.e., 1200° F.). These zeolites have a silica/alumina ratio of at least about 12 and a constraint index within the approximate range of 1 to 12. Examples of such zeolites include ZSM-5 and ZSM-11.

17 Claims, No Drawings

AROMATIC CONVERSION REACTIONS WITH ZEOLITIC CATALYST COMPOSITION OF IMPROVED SHAPE SELECTIVITY

This is a continuation-in-part of copending application Ser. No. 533,893, filed on Sept. 21, 1983, now abandoned, which is a continuation of copending application Ser. No. 454,302, filed on Dec. 29, 1982, now abandoned which is a continuation of application Ser. No. 007,871, filed Jan. 31, 1979, now abandoned. The entire disclosures of the above-identified applications are expressly incorporated herein by reference.

BACKGROUND OF THE INVENTION

1. Field of the Invention

This invention relates to a method for preparing crystalline aluminosilicate zeolite catalyst of improved shape selectivity and thermal stability, and to its use in catalytic hydrocarbon conversion processes.

2. Description of the Prior Art

The disproportionation of aromatic hydrocarbons in the presence of zeolite catalysts has been described by Grandio et al in the *Oil and Gas Journal*, Vol. 69, No. 48 (1971).

U.S. Pat. Nos. 3,126,422; 3,413,374; 3,598,878; 3,598,879 and 3,607,961 show vapor-phase disproportionation of toluene over various catalysts.

Alkylation of aromatic hydrocarbons with an olefin in the presence of a crystalline metallic aluminosilicate having uniform pore openings of about 6 to 15 Angstrom units is described in U.S. Pat. No. 2,290,607. U.S. Pat. No. 3,251,897 describes alkylation of aromatic hydrocarbons in the presence of X- or Y-type crystalline aluminosilicate zeolites, specifically such type zeolites wherein the cation is rare earth and/or hydrogen. U.S. Pat. Nos. 3,751,504 and 3,751,506 decribe vapor phase alkylation of aromatic hydrocarbons with olefins, e.g. benzene with ethylene, in the presence of a ZSM-5 type zeolite catalyst.

In these prior art processes, the xylene product produced has the equilibrium composition of approximately 24 percent para, 54 percent of meta and 22 percent of ortho.

The alkylation of toluene with methanol in the presence of a cation exchanged zeolite Y has been described by Yashima et al in the Journal of Catalysis 16, 273-280 (1970). These workers reported selective production of paraxylene over the approximate temperature range of 200° to 275° C. with the maximum yield of para-xylene in the mixture of xylenes, i.e. about 50 percent of the xylene product mixture, being observed at 225° C. Higher temperatures were reported to result in an increase in the yield of meta-xylene and a decrease in the production of para- and ortho-xylene.

Transalkylation of toluene using a catalyst of faujasite or mordenite, a Group VIII metal, such as platinum, and an additional component of arsenic, antimony, bismuth, selenium, tellurium or compounds thereof is described in U.S. Pat. No. 3,527,824.

Of the xylene isomers, i.e. ortho, meta and para-xylene, meta-xylene is the least desired product, with ortho and para-xylene being the more desired products. Para-xylene is of particular value being useful in the manufacture of terephthalic acid which is an intermediate in the manufacture of synthetic fibers, such as "Dacron". Mixtures of xylene isomers, either alone or in further admixture with ethylbenzene, generally containing a concentration of about 24 weight percent para-xylene in the equilibrium mixture, have previously been separated by expensive superfraction and multistage refrigeration steps. Such process, as will be realized, has involved high operation costs and has a limited yield.

The ZSM-5 class of zeolite catalysts have been shown to be shape selective. This shape selectivity can be further enhanced by the use of very large crystals, impregnation with Mg and P to reduce zeolite pore opening and coke selectivation. These modified zeolite catalysts have been very effective in such reactions as selective toluene disproportionation which yields predominantly p-xylene as the product and toluene-ethylene alkylation yielding primarily p-ethyltoluene. These modification procedures are quite complex and do not enhance in any way the stability of the zeolite catalyst.

U.S. Pat. Nos. 3,783,123 and 3,842,016 disclose thermally activated crystalline aluminosilicates at temperatures in excess of 900° F. for a period not substantially in excess of about 30 minutes.

SUMMARY OF THE INVENTION

In accordance with an aspect of the present invention, there is now provided a process for effecting disproportionation of a monoalkyl aromatic to produce benzene and dialkyl aromatics in which the proportion of the para-dialkyl aromatic isomer is in excess of its normal equilibrium concentration which comprises contacting a monoalkyl aromatic under conditions effective for accomplishing said disproportionation in the presence of a zeolite which has been calcined at an elevated temperature of at least 649° C., said zeolite being characterized by a silica/alumina ratio of at least about 12 and a constraint index within the approximate range of 1 to 12.

In accordance with another aspect of the present invention, there is provided a conversion process for the alkylation of a monoalkyl aromatic with olefin to produce a dialkyl aromatic in which the para-isomer is in excess of its normal equilibrium concentration which comprises contacting the monoalkyl aromatic and an olefin under conditions effective for accomplishing said alkylation in the presence of a zeolite which has been calcined at an elevated temperature of at least 640° C., said zeolite being characterized by a silica/alumina ratio of at least about 12 and a constraint index within the approximate range of 1 to 12.

According to another aspect of the invention, there is provided a process for producing xylenes in which the proportion of para-xylene isomer is in excess of its normal equilibrium concentration which comprises contacting a suitable charge stock under conditions effective for producing said xylenes in the presence of a zeolite which has been calcined at an elevated temperature of at least 649° C., said zeolite being characterized by a silica/alumina ratio of at least about 12 and a constraint index within the approximate range of 1 to 12.

DESCRIPTION OF THE SPECIFIC EMBODIMENTS

The stability of the catalyst of this invention useful in catalytic hydrocarbon conversion processes can be further enhanced by a method comprising impregnating and/or ion exchanging a crystalline aluminosilicate zeolitic starting material being in $NH_4$ or H form and having a silica/alumina ratio of at least about 12 and a constraint index, as hereinafter defined, within the approximate range of 1 to 12, with a Group IIA or Group VIII metal-containing salt, e.g. Mg, Ca, Co, Ni, in amounts between about 0.1 and 30 wt % with respect to said zeolite, preferably between about 0.5 and 15, still more preferably between about 0.6 and 6.1 wt %, and then calcining the resulting product at a temperature of at least about 649° C. or higher.

Representative magnesium and calcium- containing compounds include the acetate, nitrate, benzoate, proprionate, 2-ethylhexoate, carbonate, formate, oxylate, amide, bromide, hydride, lactate, laurate, oleate, palmitate, silicylate, stearate and sulfide forms thereof.

Reaction of the zeolite with the treating magnesium or calcium compound is effected by contacting the zeolite with such compound. Where the treating compound is a liquid, such compound can be in solution in a solvent at the time contact with the zeolite is effected. Any solvent relatively inert with respect to the treating metal compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it can be used by itself or can be used in admixture with a gaseous diluent relatively inert to the treating compound and the zeolite such as helium or nitrogen or with an organic solvent, such as octane or toluene.

The amount of metal oxide incorporated in the calcined zeolite should be at least about 0.1 percent by weight. However, it is preferred that the amount of magnesium oxide in the zeolite be at least about 0.5 percent by weight, particularly when the same is combined with a binder, e.g. 35 weight percent of alumina. The amount of metal oxide can be as high as about 30% percent by weight or more depending on the amount and type of binder present. Preferably, the amount of metal oxide added to the zeolite is between about 0.5 and about 15 percent by weight.

A charge stock utilized in the process of this invention contains as a major reactant, at least one hydrocarbon, which can be toluene, a $C_2$–$C_{10}$ olefin, xylene, and benzene.

Typical of the processes contemplated herein are the disproportionation of toluene to benzene and xylenes, wherein the proportion of para-xylene obtained is greatly in excess of its normal equilibrium concentration. Such process is effectively carried out at a temperature of between about 400° and about 750° C. at a pressure of between about 1 atmosphere and about 1000 psig utilizing a weight hourly space veolicty of between about 1 and about 20.

Another process involves the methylation of toluene by reaction of the latter with a methylating agent, preferably methanol, at a temperature between about 250° C. and about 750° C. and preferably between about 400° C. and about 600° C. The reaction generally takes place at atmospheric pressure, but the pressure may be within the approximate range of 1 atmosphere to 1000 psig. The molar ratio of methylating agent to toluene is generally between about 0.05 and about 5. When methanol is employed as the methylating agent a suitable molar ratio of methanol to toluene has been found to be approximately 0.1-2 moles of methanol per mole of toluene. With the use of other methylating agents, such as methylchloride, methylbromide, dimethylether, methylcarbonate, light olefins, or dimethylsulfide, the molar ratio of methylating agent to toluene may vary within the aforenoted range. Reaction is suitably accomplished utilizing a weight hourly space velocity of between about 1 and about 2000 and preferably between about 5 and about 1500. The reaction product consisting predominantly of para-xylene or a mixture of para- and orthoxylene, together with comparatively smaller amounts of meta-xylene may be separated by any suitable means, such as by passing the same through a water condenser and subsequently passing the organic phase through a column in which chromatographic separation of the xylene isomers is accomplished.

Another charge stock suitable for use in the process of the invention, is a stream high in $C_2$–$C_{10}$ olefin content. Thus, propylene, butenes, pentenes, hexenes, dienes such as butadiene, pentadienes, cycloolefins such as cyclopentene and cyclohexene, alkyl-substituted cycloolefins such as ethyl cyclopentene, cyclopentadiene and cyclohexadiene can be effectively converted to a high yield of para-xylene utilizing the described catalyst of the present invention, e.g., comprising a composite of a specified crystalline aluminosilicate zeolite and metal oxide. Conversion utilizing such olefin feed is carried out at a temperature within the approximate range of 300° to 700° C., a pressure between atmospheric and 1500 psig employing a weight hourly space velocity between about 1 and about 1000.

As sources of the olefin reactant either substantially pure streams of the $C_2$–$C_{10}$ olefin may be employed or refinery or chemical streams high in such reactant, i.e. generally more than 50 volume percent may be used. It is also contemplated to employ a dual catalyst bed process utilizing an initial paraffin and/or naphtha feed. In such embodiment, a charge of $C_2$ to $C_{10}$ paraffins is conducted to a first catalyst bed containing a catalyst suitable for effecting conversion of the paraffin charge to olefins. The catalyst employed in such bed is a crystalline aluminosilicate zeolite of the type hereinafter described which has not been composited with an alkaline earth oxide, e.g. HZSM-5; HZSM-11; HZSM-12; HZSM-38 or HZSM-35. These zeolites may have combined therewith a small amount of phosphorus as described in U.S. Pat. No. 3,972,832 or may have undergone prior steaming as described in U.S. Pat. No. 3,965,209. Conditions present in such bed include a temperature within the approximate range of 400° to 750° C., a pressure between atmospheric and 1000 psig and a weight hourly space velocity of between about 0.5 and about 5000. The olefins formed in such operation are then passed through a second catalyst bed, maintained under conditions described hereinabove, e.g., containing the composite catalyst of crystalline aluminosilicate zeolite and alkaline earth oxide, which zeolite has a silica to alumina ratio of at least about 12 and a constraint index within the approximate range of 1 to 12.

A still further charge stock which can be used in the process of the present invention to obtain high yields of para-xylene includes naphthenes, such as cyclopentane, cyclohexane and alkyl cyclopentanes having at least one alkyl group of 1 to 5 carbon atoms. Typical of the naphthene reactants are methyl cyclopentane, 1,2-dimethylcyclopentane, 1,3-dimethylcyclohexane. Another charge stock which can be effectively used in the present invention to selectively produce para-xylene includes paraffinic hydrocarbons having between 3 and 10 carbon atoms. Representative of such paraffins are butanes, pentanes, hexanes, heptanes, octanes and alkyl-sustituted derivatives of these paraffins. Utilizing a paraffinic and/or naphthenic charge stock, reaction conditions include, e.g., contact with the composite catalyst of crystalline aluminosilicate zeolite and metal oxide at a temperature of between about 400° to about 700° C., a pressure between about atmospheric and about 1000 psig and a weight hourly space velocity of 0.1 to 100. The catalyst has also been found useful in its selectivity for the synthesis of para-ethyltoluene, as will be seen in the examples below.

The catalysts utilized in the process of this invention comprise in one embodiment composites of alkaline earth oxide, e.g. MgO, and a crystalline aluminosilicate zeolite more fully described below. Generally, the amount of MgO in the composite catalyst will be between about 0.1 and about 30 weight percent and preferably between about 0.5 and about 15 weight percent.

The catalyst of this invention may be the product formed by impregnation of the zeolite powder or pellets with one or more alkaline earth compounds and/or ion exchanged with the same. The zeolite is preferably in the $NH_4$ or H form prior to ion exchange or impregnation. Binders such as clays, silica, or other inorganic oxides may be used. When such are used, the total catalyst composition should preferably contain at least 50 percent by weight of crystalline aluminosilicate zeolite. When the catalyst composition has the desired physical form, it is dried and then calcined at a temperature of at least about 649° C. or higher, preferably in an oxidizing atmosphere such as air.

The zeolite catalysts herein described are members of a novel class of zeolites exhibiting some unusual properties. These catalysts induce profound transformation of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalyst useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalyst, after activation, acquire an intracrystalline sorption capacity for normal hexane which is greater than that for water, i.e. they exhibit "hydrophobic" properties.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although with puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatrography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
| --- | --- |
| ZSM-5 | 8.3 |
| ZSM-11 | 8.7 |

| CAS | C.I. |
|---|---|
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H—Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5 (U.S. Pat. No. 3,702,886), ZSM-11 (U.S. Pat. No. 3,709,979), ZSM-12 (U.S. Pat. No. 3,832,449), ZSM-35 (U.S. Pat. No. 4,016,245), ZSM-38 (U.S. Pat. No. 4,046,859) and other similar materials.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline zeolites are ZSM-5, ZSM-11, ZSM-12, ZSM-38 and ZSM-35, with ZSM-5 particularly preferred.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimenter. The dry density for known structures may be calculated from the number of silicon plus aluminum atoms per 1000 cubic Angstroms, as given, e.g., on page 19 of the article on Zeolite Structure by W. M. Meir. This paper is included in "Proceedings of the Conference on Molecular Sieves, London, Apr. 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiarditel | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.2 |
| Y | .48 | 1.27 |

The conversion process described herein may be carried out as a batch type, semi-continuous or continuous operation utilizing a fixed or moving bed catalyst system. The catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the charge stock.

The following examples will serve to illustrate the process of the invention without limiting the same:

EXAMPLES 1-4

Forty-five g. of ZSM-5 extrudates (65% ZSM-5 and 35% $Al_2O_3$) were impregnated with a solution of 30 g. $Mg(OAc)_2.4H_2O$ and 25 g. $H_2O$. The impregnated product was dried overnight at 40° C. followed by two hours final calcination at 1600° F. in $N_2$ atmosphere.

The resultant catalyst was found to be very selective for the synthesis of PET (para ethyltoluene) as shown in Table 1. The Mg impregnated and calcined at 1600° F. sample has the highest selectivity to PET when compared to some catalysts prepared without the high temperature calcination, and to similar catalysts without the metal impregnation. The 1600° F. is the appoxmate temperature for Mg impregnated ZSM-5 extrudates at which it has been found by the DTA (differential thermal analysis) that a solid state exothermic reaction occurs. The reaction is thought to be between Mg and ZSM-5. Similar reactions between other metal compounds such as Ca, Zn, Cu, Pb and others are expected. Results are listed in Table 1 below.

The as synthesized zeolite powder was pressed into thin tablets which was calcined in $N_2$ for 3 hours at 1000° F. and followed by $NH_4NO_3$ exchange to reduce its Na to less than 0.01% weight. The exchanged sample was sized to 14/25 mesh and air calcined for 3 hours at 1000° F. The $\alpha$ activity of this finished catalyst was found to be 480.

EXAMPLE 6

The finished catalyst of Example 5 was steamed with 100% steam at 900° F., 100 psig pressure for 48 hours. The steamed catalyst has an alpha activity of 3.8.

EXAMPLE 7

TABLE I

| | PET TEST RESULTS | | | | |
|---|---|---|---|---|---|
| Example | 1 | 2 | 3 | 4 | |
| Zeolite | ZSM-5 | → | → | → | |
| $SiO_2/Al_2O_3$ | 70 | 70 | 70 | 70 | |
| Binder | 35% $Al_2O_3$ | 35% $Al_2O_3$ | — | 40% clay | |
| Impregnation | $Mg(OAc)_2 \cdot 4H_2O$ | → | None | None | |
| Mg. Wt. % | 4 | 3.3 | — | — | |
| Calcination 2 hrs | (T-2) at 1600° F. | T-3-1000° F. | T-3-1000° F. | T-2-1600° | |
| Test Conditions | | | | | |
| Temperature, °F. | 800 | 800 | 800 | 800 | 800 |
| Toluene, g/Hr | 26 | 13 | 26 | 26 | 26 |
| Ethylene, g/Hr | 1.125 | 0.563 | 1.125 | 1.125 | 1.125 |
| TOS, Hr. | 1 | 2 | 1 | 1 | 1 |
| Test Results | | | | | |
| Toluene Conv., % | 6.23 | 9.93 | 14.00 | 13.80 | 12.68 |
| Total ET Product, % | 5.99 | 9.68 | 12.68 | 12.10 | 11.50 |
| Normalized ET % | | | | | |
| PET | 99.2 | 94.9 | 33.6 | 32.7 | 52.7 |
| MET | 0.8 | 5.1 | 63.1 | 63.6 | 46.6 |
| OET | 0 | 0 | 3.3 | 3.7 | 0.7 |

Catalytic cracking activity is indicated by the weight percent conversion of hexane to lower boiling $C_1$–$C_5$ hydrocarbons, while isomerization activity is indicated by weight percent conversion to hexane isomers. Cracking activity is also indicated quantitatively by the term alpha ($\alpha$) which is an indication of the relative catalytic cracking activity of the catalyst compared to a standard catalyst, $\alpha$ is the relative rate constant (rate of n-hexane conversion per unit volume of oxides composition per unit time). It is based on the activity of highly active silica alumina cracking catalyst taken as $\alpha = 1$.

The $\alpha$-test is further described in a letter to the editor entitled "Superactive Crystalline Aluminosilicate Hydrocarbon Cracking Catalysts" by P. B. Weisz and J. N. Miale, Journal of Catalysis, Vol. 4, pp. 527-529 (August 1965).

EXAMPLE 5

A ZSM-5 sample of 40 $SiO_2/Al_2O_3$ ratio was prepared into hydrogen form by the standard procedure.

The fresh H form catalyst in Example 5 was impregnated with $Mg(NO_3)_2$ solution to 2.84% Mg. The catalyst was steamed with 100% steam at 900° F. 100 psig for 48 hours. The $\alpha$ activity of the final catalyst was 11.7.

EXAMPLE 8 (8a and 8b)

The fresh H form catalyst in Example 5 was ion exchanged with $Mg(NO_3)_2$ solution to 1.4% Mg. The exchanged catalyst was calcined in air at 1600° F. for 3 hours. Samples of the calcined catalyst were steamed with 100% steam at 900° F. 100 psig for 24 and 48 hours, respectively. The $\alpha$ activities of the steamed catalysts are 31 and 23, respectively.

The results of Examples 5–8 are summarized in Table 2. The resulted steam stability of Mg addition/combining with high temperature calcination is quite obvious.

TABLE II

| | N—HEXANE CRACKING ACTIVITY TEST | | | | | |
|---|---|---|---|---|---|---|
| Example | 5 | 6 | 7 | 8a | | 8b |
| Zeolite | ZSM-5 | → | → | → | | → |
| Metal | 0 | 0 | Mg | Mg | | Mg |
| Method of Incorp. | — | — | Impr. | Ion Exchange | | — |
| Wt % Metal | — | — | 2.84 | 1.40 | | 1.40 |
| $SiO_2/Al_2O_3$ of zeolite | 40 | 40 | 40 | 40 | | 40 |
| binder | — | — | — | — | | — |
| Steaming & Others | fresh | | | | | |
| Temp, °F. | 1000 | 900 | 900 | 1600 | 900 | 1600 | 900 |
| Pressure, psig | — | 100 | 100 | 0 | 100 | 0 | 100 |
| Time, Hr | 3 | 48 | 48 | 3 | 24 | 3 | 48 |
| Steam, % | Air | 100 | 100 | Air | 100 | Air | 100 |
| Test Condition | | | | | | |

TABLE II-continued

| | N—HEXANE CRACKING ACTIVITY TEST | | | | |
|---|---|---|---|---|---|
| Example | 5 | 6 | 7 | 8a | 8b |
| Catalyst Vol, cc. | 0.25 | 1.0 | 1 | 1 | 1 |
| Carrier gas, cc/min | 18 | 18 | 18 | 18 | 18 |
| n $C_6$ rate, cc/min | 1 | 1 | 1 | 1 | 1 |
| Temp, °F. | 1000 | 1000 | 1000 | 1000 | 1000 |
| Time on Steam, min | 5 | 5 | 5 | 5 | 5 |
| LHSV | 4 | 1 | 1 | 1 | 1 |
| Test Results | | | | | |
| Conv. of n $C_6$, wt % | 96.8 | 10.4 | 28.5 | 58.6 | 48.6 |
| $C_5^-$ Products, wt % | 78.4 | 10.4 | 28.5 | 57.1 | 47.6 |
| Total Aromatics, wt % | 18.4 | — | 0.1 | 1.5 | 1.1 |
| $k \times 10^3$, $sec^{-1}$ | 4800 | 38.7 | 118 | 310 | 235 |
| $\alpha$ | 480 | 3.8 | 11.7 | 30.7 | 23.2± |

The following examples illustrate Mg, Ca, Co, and Ni-impregnated catalysts.

EXAMPLE 9

The Mg impregnated catalyst of Example 1 was also calcined at 1300° F. for one hour. The resultant catalyst was also selective for the synthesis of PET. Under the same test conditions, as Example 1, the toluene conversion was 11.15%, ethyltoluene (ET) in product was 10.23%, and PET selectivity was 94.53%.

EXAMPLE 10

The Mg impregnated catalyst of Example 1 was also calcined at 1400° F. for 1 hour. The resultant catalyst was also selective for the synthesis of PET. Under the same test conditions the toluene conversion was 10.58% and the selectivity to PET was 95.9%.

EXAMPLE 11

The Mg impregnated catalyst of Example 1 was calcined at 1200° F. for 2 hours. The resultant catalyst was less active but still selective for the synthesis of PET. The toluene conversion was 8.16% and PET selectivity was 91.8%.

EXAMPLE 12

Twenty grams of ZSM-5 extrudates, 70/1 $SiO_2/Al_2O_3$ (65% ZSM-5 and 35% $Al_2O_3$) were impregnated with a $Ca(NO_3)_2.3H_2O$ melt (~100° C.) for 0.5 hour, then the excess was drained off. The soaked extrudates were then dried overnight at room temperature. The final calcination was carried out in flowing $N_2$, holding at 900° F. for 1 hour and then at 1500° F. for another hour. The resultant catalyst was selective for the synthesis of PET. The toluene conversion was 2.36% and PET selectivity was 100%.

EXAMPLE 13

Twenty grams of ZSM-5 extrudates, $SiO_2/Al_2O_3=70$, (65% ZSM-5 and 35% $Al_2O_3$) were soaked in $Co(NO_3)_2.6H_2O$ melt (~100° C.) for 0.5 hour, then the excess molten salt was drained. The catalyst was dried at room temperature overnight and was then calcined in flowing $N_2$ at 900° F. for 1 hour and at 1500° F. for 1 hour. The resultant catalyst was active for the synthesis of PET. The toluene conversion was 6.83% and PET selectivity was 67%. Results of the foregoing examples are summarized in Table III.

TABLE III

| | PET TEST RESULTS | | | | |
|---|---|---|---|---|---|
| EXAMPLE | 9 | 10 | 11 | 12 | 13 |
| Zeolite | ZSM-5 | → | → | → | → |
| $SiO_2/Al_2O_3$ | 70 | 70 | 70 | 70 | 70 |
| Binder | 35% $Al_2O_3$ | 35% $Al_2O_3$ | 35% $Al_2O_3$ | 35% $Al_2O_3$ | 35% $Al_2O_3$ |
| Impregnation | $Mg(OAc)_2.4H_2O$ | → | None | $Ca(NO_3)_2.3H_2O$ | $Co(NO_3)_2$ |
| Wt % | 4% Mg | 4% Mg | — | 6% Ca | 9% Co |
| Calcination | T-1 1300° F. | T-1 1400° F. | T-2 1200° F. | T-1 900° F. and T-1 1500° F. | T-1 900° F. T-1 1500° F. |
| Test Condition | | | | | |
| Temperature, °F. | 800 | 800 | 800 | 800 | 800 |
| Toluene, g/Hr | 26 | 26 | 26 | 26 | 26 |
| Ethylene, g/Hr | 1.125 | 1.125 | 1.125 | 1.125 | 1.125 |
| TOS, Hr. | 1 | 1 | 1 | 1 | 1 |
| Test Results | | | | | |
| Toluene Conv., % | 11.15 | 10.58 | 8.16 | 2.4 | 6.8 |
| Total ET Product, % | 10.23 | — | — | — | — |
| Normalized ET % | | | | | |
| PET | 94.53 | 95.9 | 91.8 | 100 | 67 |
| MET | — | — | — | — | — |
| OET | — | — | — | — | — |

EXAMPLE 14

To further demonstrate the stability of the ZSM-5 samples which have been treated by metal (Ni) impregnation and high temperature calcination (1600° F.). The following samples were prepared: A $SiO_2/Al_2O_3$ ratio of 70 ZSM-5 extrudates (65% ZSM-5 and 35% $Al_2O_3$). One % Ni by weight was added to the extrudates which were then calcined for 3 hours in air at the following temperatures: 1200° F., 1400° F., 1600° F. and 1800° F. The $\alpha$ values of the above samples were 203, 133, 80 and 7, respectively.

The above calcined samples were steamed for 48 hours at 900° F., 100 psig, 100% steam and tested for values again. The corresponding $\alpha$ values were 6, 13, 19 and 3, respectively. The 1600° F. calcined samples is more stable than others. Results are summarized below.

| Ni Added ZSM-5 Extrudates (SiO$_2$/Al$_2$O$_3$ = 70, 35% Al$_2$O$_3$) Ni 1% by weight based on Extrudate | | | | |
|---|---|---|---|---|
| Calcination Temp °F. (in air) | 1200 | 1400 | 1600 | 1800 |
| α Value | 203 | 133 | 80 | 6.8 |
| Steam Treatment T-48-900° F., 100 psig, 100% steam | | | | |
| α Value (after steaming) | 6.3 | 13.3 | 19.0 | 2.5 |

EXAMPLES 15–20

A ZSM-5 catalyst, having SiO$_2$/Al$_2$O$_3$ ratio of at least 12 and a constraint index of 1–12, was prepared by extruding a composite mixture of 65 weight % (wt %) ZSM-5 (having a crystal size of 5-7 microns) and 35% alumina (Al$_2$O$_3$). Extrudates were calcined in the nitrogen (N$_2$) atmosphere at 1000° F. for about 3 hours to decompose the organics in zeolite. Subsequently, the calcined extrudates were ion exchanged with an aqueous ammonia nitrate (NH$_4$NO$_3$) solution (containing about 8% wt. of NH$_4$NO$_3$) to reduce the sodium (Na) content to less than 0.02 wt % Na level. The thus-obtained ammonium ZSM-5 catalyst was then modified by ion exchange and impregnation to prepare various Group IIA and Group VIII-metal containing forms of ZSM-5 catalysts. The metal-containing catalysts were prepared in accordance with the procedure of Example 15, set forth below. The hydrogen form of the ZSM-5 zeolite catalyst was prepared by calcining the aforementioned ammonia form of ZSM-5 catalyst for three (3) hours in the nitrogen atmosphere at 1600° F.

Thirty grams of the ion-exchanged sample was impregnated with an aqueous solution comprising about 60% wt of nickel nitrate [Ni(NO$_3$)$_3$.6H$_2$O] for two (2) hours at ambient temperature. The impregnated product was drained, then dried at 230° F. and then calcined by heating in air at a temperature of 1600° F. for three (3) hours. The thus-prepared catalyst had a calculated nickel content of 13% wt.

Catalysts were impregnated with other metals of Groups IIA and VIII, namely iron (Fe), strontium (Sr), calcium (Ca) and barium (Ba) in Examples 16–20 in the manner described above with the aqueous solutions comprising about 60% wt of the respective metals. The resulting catalysts had the following calculated amounts of the respective metals in the final catalyst.

| | Type and Amount Of Metal On Catalyst |
|---|---|
| Example 16 | Fe - 13% |
| Example 17 | Sr - 15% |
| Example 18 | Ca - 10% |
| Example 19 | Ba - 20% |
| Example 20 | H$_2$ - form |

The catalysts of Examples 15–20 were then used to promote alkylation of toluene with ethylene (C$_2$=);

Table IV summarizes the reaction conditions and toluene conversion results obtained from the ethylene alkylation of toluene experiments described above.

TABLE IV

| Example | 15 | 16 | 17 | 18 | 19 | 20 |
|---|---|---|---|---|---|---|
| Modifying Compound | Ni | Fe | Sr | Ca | Ba | H$_2$-form |
| Amount of modifying compound, wt % | 13 | 13 | 15 | 10 | 20 | — |
| Test Conditions | | | | | | |
| Temperature, ° F. | 810 | 810 | 810 | 810 | 810 | 810 |
| Weight Hourly Space Velocity (WHSV) of: | | | | | | |
| ethylene | 1 | 1 | 1 | 1 | 1 | 1 |
| toluene | 29 | 29 | 29 | 29 | 29 | 29 |
| hydrogen | 0.25 | 0.25 | 0.25 | 0.25 | 0.25 | 0.25 |
| Pressure, psig | 100 | 100 | 100 | 100 | 100 | 100 |
| Length of alkylation test, hrs | 3 | 3 | 3 | 3 | 3 | 3 |
| Test Results | | | | | | |
| Toluene to Ethyltoluene (ET) Conversion, % | 3.5 | 4.9 | 0.3 | 0.1 | 0.67 | 10.1 |
| Ethylene to Ethyltoluene Conversion, % | 31.0 | 43.9 | 2.6 | 0.6 | 5.9 | 89.9 |
| Selectivity to para-ET product*, % | 85.2 | 90.4 | 100 | 100 | 100 | 75.4 |

*Selectivity was calculated by dividing the amount of the para-ET product produced by the total amount of all ET isomers produced.

EXAMPLE 21

Ten grams of a 70 mole ratio SiO$_2$/Al$_2$O$_3$ ZSM-5 of Na form was exchanged with 500 ml of 10% calcium acetate solution at 212° F. for three times of one hour each. Then the catalyst was filtered, water washed and dried. The catalyst was analyzed and found to contain 0.08% wt sodium (Na) and 0.9% wt calcium (Ca).

Twenty milligrams of the above sample was tested on a R.L. Stone Differential Thermal Analyzer (DTA) using a high-temperature sample holder made of palladium (Pd) and thermocouple of platinum-rhenium (Pt-Rh). The heating rate was 20° C./min and the purge gas was helium, at a flow rate of 0.1 ft$^3$/hr. An exothermic peak was detected at 780°–800° C. (1436°–1472° F.) and was assigned to stabilization. The lattice collapse occurred at 1350° C. (2462° F.) and it compared favorably with 1250° C. (2282° F.) for lattice collapse temperature of HZSM-5 and NaZSM-5 forms.

EXAMPLE 22

Ten grams of a 70 SiO$_2$/Al$_2$O$_3$ mole ratio ZSM-5 of Na form was exchanged with 500 ml of 10% Ba(NO$_3$)$_2$ solution at 212° F. for three times of 4 hours each. The sample was filtered, water-washed and dried. The sample was analyzed and found to contain 0.1% Na and 2.4% Ba.

Twenty milligrams of the dried BaZSM-5 was tested on a DTA analyzer using the procedure described in Example 21. The lattice collapse temperature was 1320° C. (2408° F.).

EXAMPLE 23

Ten grams of NaZSM-5 of 70 SiO$_2$/Al$_2$O$_3$ mole ratio was exchanged wih 500 ml of 10% Co (NO$_3$)$_2$ solution, once at 212° F. for 4 hours and once at 350° F. in an autoclave for 16 hours. The catalyst was filtered, washed and dried.

The lattice collapse temperature of CoZSM-5 on DTA thermogram was found to be 1260° C. (2300° F.).

EXAMPLE 24

Ten grams of NaZSM-11 of 40 $SiO_2/Al_2O_3$ mole ratio was exchanged wih 500 ml of 10% $Mg(NO_3)_2$ solution three times of 4 hours each at 212° F. The catalyst was filtered, washed and dried. The Mg content of this sample was found to be 0.7 wt %. The MgZSM-11 was tested by the procedure described in Examples 21–23, above. The lattice collapsing temperature was about 1300° C. (2372° F.) for MgZSM-11 compared with 1250° C. (2282° F.) for NaZSM-11.

What is claimed is:

1. A conversion process for the alkylation of a monoalkyl aromatic with an olefin to produce a dialkyl aromatic in which the para-isomer is in excess of its normal equilibrium concentration which comprises contacting said monoalkyl aromatic and said olefin under conditions effective for accomplishing said alkylation in the presence of a zeolite which has been calcined at an elevated temperature of at least 649° C., said zeolite being characterized by a silica/alumina ratio of at least about 12 and a constraint index within the approximate range of 1 to 12.

2. A process according to claim 1, wherein said monoalkyl aromatic is toluene, said olefin is ethylene and said dialkyl aromatic is ethyltoluene.

3. A process according to claim 1, wherein said crystalline zeolite is characterized by a silica/alumina ratio in excess of 30.

4. A process according to claim 1, wherein said crystalline zeolite is ZSM-5.

5. A process according to claim 1, wherein a Group IIA or Group VIII metal containing compound is incorporated into said zeolite by impregnation and/or ion-exchange in an amount of at least about 0.1 wt % with respect to said zeolite, as the oxide, then the resultant metal containing zeolite is calcined at said elevated temperature of at least about 649° C. to bring about a solid state reaction between said metal and said zeolite.

6. A process according to claim 1, wherein a binder is composited with said zeolite.

7. A process according to claim 5, wherein magnesium addition is accomplished as a results of contact of the crystalline zeolite with a magnesium compound.

8. A process according to claim 7, wherein magnesium oxide is present in an amount of between about 0.1 and about 30 weight percent.

9. A process according to claim 8, wherein said magnesium oxide is present in an amount of between about 0.5 and about 15 weight percent.

10. A process according to claim 1, wherein the alkylation conditions include a temperature of between about 390° F. and about 1400° F., a pressure between atmospheric and about 1000 psig and a weight hourly space velocity between about 0.08 and about 20.

11. A process according to claim 1, wherein the zeolite is combined in an amount between about 1 and about 90 weight percent in a binder therefor.

12. A process according to claim 11, wherein said binder is alumina.

13. A process according to claim 1, wherein the zeolite is predominately in the hydrogen form.

14. A process according to claim 4, wherein the ZSM-5 zeolite is predominately in the hydrogen form.

15. A process according to claim 2, wherein the crystalline zeolite is ZSM-5.

16. A process according to claim 15, wherein the ZSM-5 zeolite is predominately in the hydrogen form.

17. A process according the claim 5, wherein said Group IIA or Group VIII metal is present in an amount between about 0.1 and 30 wt %.

* * * * *